United States Patent
Stengele

(10) Patent No.: US 7,432,368 B2
(45) Date of Patent: Oct. 7, 2008

(54) PHOTOLABILE PROTECTING GROUPS

(75) Inventor: Klaus-Peter Stengele, Pleiskirchen (DE)

(73) Assignee: Roche NimbleGen, Inc., Madison, WI (US)

( * ) Notice: Subject to any disclaimer, the term of this patent is extended or adjusted under 35 U.S.C. 154(b) by 498 days.

(21) Appl. No.: 11/109,873

(22) Filed: Apr. 20, 2005

(65) Prior Publication Data

US 2005/0272076 A1 Dec. 8, 2005

(30) Foreign Application Priority Data

Apr. 20, 2004 (DE) .......... 10 2004 019 098

(51) Int. Cl.
*C07H 21/00* (2006.01)
*A01N 43/04* (2006.01)
*A61K 31/70* (2006.01)

(52) U.S. Cl. ............ 536/25.32; 536/18.5; 536/25.3

(58) Field of Classification Search ............ None
See application file for complete search history.

(56) References Cited

U.S. PATENT DOCUMENTS

| 5,763,599 | A | 6/1998 | Pfleiderer et al. |
| 6,426,184 | B1 | 7/2002 | Gao et al. |
| 6,756,492 | B1 | 6/2004 | Beier et al. |

FOREIGN PATENT DOCUMENTS

| DE | 4444996 | 6/1996 |
| DE | 19915867 | 10/2000 |
| DE | 20210018 | 1/2003 |
| DE | 69909972 | 5/2004 |
| WO | WO 9839348 | 9/1998 |
| WO | WO 0031588 | 6/2000 |
| WO | WO 03074542 | 9/2003 |

*Primary Examiner*—Patrick T Lewis
(74) *Attorney, Agent, or Firm*—Millen, White, Zelano & Branigan, P.C.

(57) ABSTRACT

The present invention relates to novel nucleoside derivatives of general formula (I)

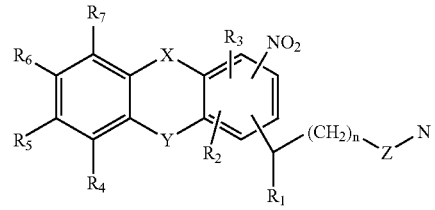

wherein $R^1$=H, halogen, $NO_2$, CN, $OCH_3$, an alkyl, alkoxy or alkoxyalkyl residue having 1 to 4 C atoms, preferably a methyl, ethyl, propyl or butyl residue or an optionally substituted aryl residue or aliphatic acyl residue having 2 to 5 atoms, $R^2$ to $R^7$=H, $NO_2$, CN, $OCH_3$, a branched or unbranched alkyl, alkoxy or alkoxyalkyl residue having 1 to 5 C atoms or an optionally substituted aryl residue or an aliphatic acyl residue having 2 to 5 atoms, X is the group C=O or C=S, Y=S, O, NR', C(R')$_2$, wherein R' is H, or a branched or unbranched alkyl residue having 1 to 5 C atoms or an optionally substituted aryl residue, Z=$SO_2$, OCO, OCS, SCS, and N is a nucleotide.

9 Claims, 4 Drawing Sheets

PHOTOLABILE PROTECTING GROUPS

The present invention relates to nucleoside derivatives having photolabile protecting groups, a process for producing the same and the use thereof for the production of DNA chips by spatially addressed, light-controlled nucleotide synthesis on solid substrates.

The facile selective cleavage of functional groups from molecules plays an important role in many fields of chemistry and biology, in particular e.g. in the synthesis of major chemical units, such as the synthesis of polymers, natural substances, etc.

In this connection, particularly reactive groups, for example, which can affect or interfere the respective intended linkage of two molecules by undesired secondary reactions, are selectively "masked" or protected for some time by chemically or physically recleavable functional protecting groups so that they are not involved in the desired linkage reaction.

The use of major combinatory libraries of binding partners, immobilized on a substrate, of the biomolecules offered in solution are of major advantage for a comparative study of the molecular detection between biomolecules of equal or different structural classes. The term "biomolecules" is understood to mean by a person skilled in the art in particular compounds belonging to the classes of nucleic acids and their derivatives, proteins, peptides and carbohydrates.

Major combinatory libraries which use the principle of mutual molecular detection are of great significance in particular for the analytics of nucleic acids. For example in medicine and pharmaceutical research, DNA chips, i.e. so called microarrays of regions on a glass or polymer substrate of immobilized DNA or any selected oligonucleotides (S. P. A. Fodor, Science 277 (1997) 393, DNA Sequencing Massively Parallel Genomics) have been used for some time.

Here, DNA chips again adopt an important role in genetic analytics and diagnostics. The most widely spread technology for the production of such DNA chips is the spatially addressed, parallel, light-controlled oligonucleotide synthesis on solid substrates (see e.g. S. P. A. Fodor et al., Nature 364 (1993) 555, Multiplexed Biochemical Arrays with Biological Chips) using photolabile protecting groups, i.e. protecting groups for reactive functionalities of nucleoside and/or nucleotide building blocks which can usually be recleaved selectively under the influence of U.V. light with a specific wavelength so as to provide the protected functionalities for further reaction.

In this connection, the above mentioned so-called photolithographic technique serves for the production of the DNA chips. The synthetic design of the desired oligonucleotide chains on the substrate is controlled by suitable labile, preferably photolabile, protecting groups which e.g. upon exposure (electromagnetic radiation within the UV/VIS range is usually used for this purpose) release the linkage site for the respectively next nucleotide. By means of these photolabile protecting groups a combinatory strategy can be developed using a spatial selective exposure. Using this strategy it is possible to produce extremely dense, spatially addressable microarrays of oligonucleotides whose number grows exponentially with the number of synthesis cycles. With a currently achievable area of less than 25 $\mu m^2$ for each element, theoretically over $10^6$ probe regions can be accommodated per 1 $cm^2$. Exposure is currently carried out by means of micromirror arrays (S. Singh-Gasson et al., Nature Biotechn. 17 (1999) 974, Maskless Fabrication of Light Directed Oligonucleotide Microarrays using a Digital Micromirror Array) as used in the digital projection technology. The time-consuming and expensive production of exposure masks is thus dispensed with, enabling a faster production of the DNA chips by means of the photolithographic technique.

Therefore, a central aspect of photolithographic synthesis relates to the kind of these photolabile protecting groups which are used in various chemical variants in organic and bioorganic chemistry (V. N. R. Pillay, Photolithic Deprotection and Activation of Functional Groups; in: Organic Photochemistry, Vol. 9, ed. A. Padwa (Marcel Dekker, New York and Basel, 1987) page 225 et seq.). Photolabile protecting groups on the basis of the 2-nitrobenzyl group are most widely used. (J. E. T. Correy and E. R. Trenton, Caged Nucleotides and Neurotransmitters; in: Biological Application of Photochemical Switches, in: Bioorganic Photochemistry Series, Vol. 2, ed. Harry Morrison (Wiley Interscience, 1993), page 243 et seq.).

For the production of DNA Chips, e.g. for protecting the terminal OH group in the oligonucleotide synthesis from the 3' to 5' or 5' to 3' end, the MeNPOC (α-methyl nitropiperonyloxycarbonyl) protecting group is currently preferred among the 2-nitrobenzyl type protecting groups which has been the standard protecting group in the DNA chip production for some time now (S. P. A. Fodor et al., Science 251 (1991), 767, Light Directed, Spatially Addressable Parallel Chemical Synthesis).

The formation of the aromatic nitrosoketone after the irradiation, which represents a very reactive leaving group, is unfavorable for this kind of protecting groups. Thus, undesired secondary and successive reactions occur which often cause defects in the nucleotide synthesis of the resulting oligonucleotide and/or polynucleotide. For example, such successive and secondary reactions form because a part of the existing photolabile protecting groups per se is excited by the electromagnetic radiation and, in the excited state, may cause a plurality of undesired secondary reactions, such as degradation, intramolecular and intermolecular rearrangements, etc.

Furthermore, 2-(2-nitrophenyl)ethoxycarbonyl compounds are known for the production of DNA chips. The protecting groups thereof are cleaved as 2-nitrostyrene derivatives (DE-PS 44 44 996, DE-PS 196 20 170 and U.S. Pat. No. 5,763,599). As a result of the cleavage of generally slightly low-reactivity 2-nitrostyrenes with respect to interfering secondary reactions, these compounds are somewhat less interference-prone than the above mentioned compounds.

For a short time, the DMBOC group (3',5'-dimethoxybenzoinyloxycarbonyl group) has been used as a protecting group (M. C. Pirrung et al., J. Org. Chem. 63 (1998), 241, Proofing of Photolithographic DNA Syntheses with 3',5'-dimethoxybenzoinyloxycarbony-protected deoxynucleosidedeophosphoramidites) in the selective polynucleotide synthesis.

Further protecting groups used thus far are NPPOC (2-(2-nitrophenyl)propyloxycarbonyl), MeNPPOC (2-(3,4-methylenedioxy-2-nitrophenyl)propyloxycarbonyl), MeNPOC (2-(3,4-methylenedioxy-2-nitrophenyl)oxycarbonyl), DMBOC (dimethoxybenzoinylyloxycarbonyl), NPES (2-(2-nitrophenyl)ethylsulfonyl) and NPPS (2-nitrophenyl)propylsulfonyl), for example.

Currently used photolabile protecting groups still show no satisfactory results with respect to the error rate of the DNA chips synthesized in this way (D. J. Lockheart and E. A. Winseler, Nature 405 (2000) 827, Genomics, Gene Expression and DNA Arrays). The cleavage of the protecting groups does not proceed in a sufficiently complete manner since said groups usually only have a minor absorbability for the employed UV/VIS wavelengths. In addition, interfering secondary reactions having undesired reaction products occur in this connection so that a major part of the oligonucleotides on the DNA chips cannot be used.

Moreover, the reaction rate of the cleavage reaction is unsatisfactorily long for the protecting groups known thus far since the currently known photolabile protecting groups require irradiation periods of several minutes with the common irradiation intensities with the 365 nm line of a mercury vapor lamp to be able to react quantitatively.

The object of the present invention therefore consisted of providing nucleoside derivatives having new photolabile protecting groups, which do not show the above mentioned drawbacks of the prior art and whose protecting groups can be cleaved particularly rapidly and without causing secondary reactions.

This object is achieved by providing nucleoside derivatives which contain photolabile protecting groups and have the structural motif

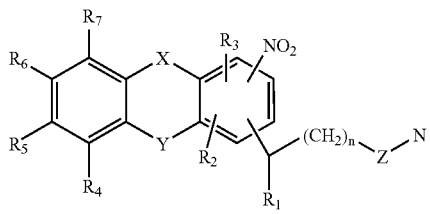

wherein $R^1$ is H, halogen, $NO_2$, CN, $OCH_3$, an alkyl, alkoxy or alkoxyalkyl residue having 1 to 4 C atoms, or an optionally substituted aryl residue or aliphatic acyl residue having 2 to 5 atoms, $R^2$ to $R^7$ are H, $NO_2$, CN, $OCH_3$, a branched or unbranched alkyl, alkoxy or alkoxyalkyl residue having 1 to 5 C atoms, preferably a methyl, ethyl, propyl, butyl or pentyl residue or an optionally substituted aryl residue or an acyl residue RCO, wherein R is an aliphatic residue having 2 to 5 carbon atoms, X represents the group C=O or C=S, Y=S, O, NR', $C(R')_2$, wherein R' is H or a branched or unbranched alkyl residue having 1 to 5 C atoms or an optionally substituted aryl residue, $Z=SO_2$, OCO, OCS, SCS, CO or CS, n=0, 1, 2 or 3 with the proviso that when n=0, Z is selected from CO, CS, $SO_2$, and N is selected from 3' or 5' substitutable nucleosides such as

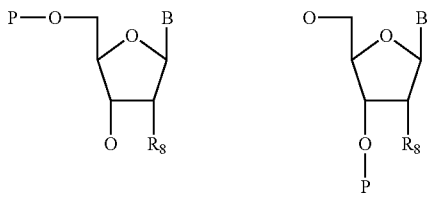

wherein P=H or a protecting group common in the nucleotide chemistry or a reactive group common for the production of oligonucleotides, B=adenine, cytosine, guanine, thymine, uracil, 2,6-diaminopurine-9-yl, 5-methylcytosinyl-1-yl, 5-amino-4-imidazolecarboxylic acid-1-yl or 5-amino-4-imidazolecarboxylic acid amide-3-yl, wherein, when B=adenine, cytosine or guanine have the primary amino function and optionally a temporary or permanent protecting group or thymine or uracil optionally has a permanent protecting group at the $O^4$ position, $R^8$=H, OH, halogen, OR' or SR', wherein R' is as defined above or an aliphatic acyl residue having 2 to 5 atoms and a protecting group common in nucleotide chemistry.

The alkyl, alkoxy or alkoxyalkyl group of residues $R^1$ to $R^8$ may be linear or branched, substituted (only with one or several halogen atoms in toto) or unsubstituted and saturated or unsaturated. A bridge-type bond may exist between the residues, e.g. via a methylene group, so that there is another ring function. The same applies analogously to the acyl or aryl group of residues $R^1$ to $R^8$. Here, the substituents in consideration are alkyl groups along with halogen atoms. Preferred alkyl residues are methyl, ethyl, n-propyl, n-butyl, iso-propyl, tert-butyl residues. Preferred alkoxy residues are the methoxy, ethoxy or tert-butoxy residues. Preferred aliphatic acyl residues are formyl, acetyl, propionyl or butyryl. Preferred (hetero)aryl residues are the phenyl, thienyl, thiophenyl, furyl, furanyl, pyranyl, pyrrolyl, imidazolyl, pyrazolyl, pyridyl, pyrazinyl, pyrimidinyl, pyrazinyl, pyridazinyl, thiazolyl, oxazolyl, indolyl, pyrrolinyl, imidazolinyl, pyrazolinyl, thiazolinyl, triazolyl, tetrazolyl group and resulting fused rings.

At position P, "a reactive group common for the production of oligonucleotides" is a phosphitamide group, for example. Of course, phosphodiesters, phosphotriesters or H-phosphonates can also be used in place of a phosphite amide.

At positions P and $R^8$, the expression "a protecting group common in nucleotide chemistry" is in particular in $R^8$ a H (DNA) or O (RNA) protecting group such as the common O-alkyl, O-alkenyl, O-acetal or O-silylether protecting groups. Preferred protecting groups are O-methyl or O-ethyl residues, O-allyl residues, O-tetrahydropyranyl or O-methoxytetrahydropyranyl residues and O-t-butyldimethylsilyl residues, dimethoxytrityl (DMT) or dansyl residues.

The protecting groups optionally occurring permanently at bases B are based preferably on acyl protecting groups. Above all phenoxyacetyl, tert-butylphenoxyacetyl, isobutyryl, acetyl, benzoyl, allyloxycarbonyl, phthaloyl, dansylethyloxycarbonyl, 2-(4-nitrophenyl)ethoxycarbonyl or dimethylformamidino residues are preferred. In the case of adenine, cytosine and guanine, preferably phenoxyacetyl, tert-butylphenoxyacetyl, acetyl or 2-(4-nitrophenyl)ethoxycarbonyl groups for the production of the exocyclic amino functions are concerned. The $O^6$ position of guanine can optionally also be protected by a protecting group 2-(4-nitrophenylsulfonyl)ethyl or 2-(4-nitrophenyl)ethyl. Likewise the $O^4$ position of thymine or uracil may have a protecting group such as 2-(4-nitrophenylsulfonyl)ethyl or 2-(4-nitrophenyl)ethyl.

Within the scope of the present invention halogen denotes F, Cl, Br, I, the latter three being preferred. The production of the nucleoside derivatives according to the invention is shown by way of example in FIG. 2, to which reference is made below. The mention of certain halogen and alkyl substitutions always includes equivalents having equal effects, e.g. "chloro" does not rule out that the corresponding iodine or bromine compounds can be used as well. The same applies to "methyl" which also includes the corresponding other low alkyl compounds, such as ethyl, propyl or butyl.

With respect to the known derivatives, the nucleoside derivatives according to the invention have the surprising advantage that the protecting group according to the invention can be cleaved more rapidly and effectively even upon irradiation with visible light at wavelengths above 380 nm, preferably above 390 nm and more preferably above 400 nm.

Based on the present invention, it is particularly important that with the protecting group according to the invention a nitro group and the group linking the nucleoside with the ring system are placed on the anthracene skeleton in the o-position with respect to each other to be able to carry out a β-elimination reaction on cleavage.

This refers to all the o-substitution patterns at positions 1 to 4 of the ring system according to the invention. This concerns in particular the following derivatives:

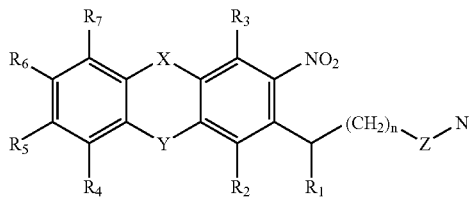

1a

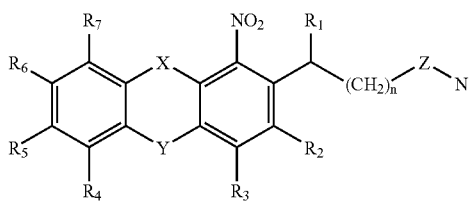

1b

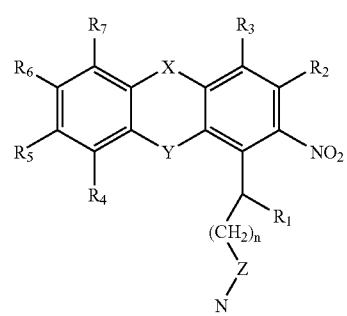

1c

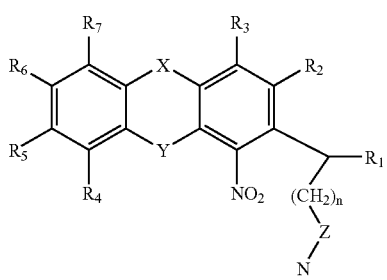

1d

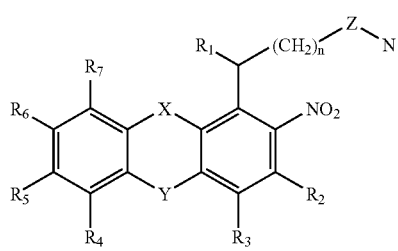

1e

-continued

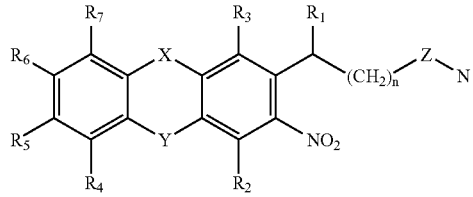

1f wherein in formulae 1a to 1f the substituents have the above mentioned meanings.

The photolabile 3' or 5' nucleosides according to the invention can be used for the photolithographic nucleic acid chip synthesis. The person skilled in the art is sufficiently familiar with processes for this purpose.

The use of the protecting group or the nucleoside derivative according to the invention advantageously permits the use of particularly long-waved light in the light-controlled synthesis of oligonucleotides or nucleic acid chips. In this connection, wavelengths above 380 nm, preferably above 390 nm and more preferably above 400 nm are preferred.

"Substrate" is understood to mean chemical compounds, preferably oligonucleotides, proteins, peptides, carbohydrates (sugar), which may enter into a covalent chemical bond with the compound according to the invention. However, the term substrate also comprises surface-functionalized carrier materials, such as glass, polymers, metal, ceramics, etc.

According to the invention the term "nucleotide" is preferably understood to mean oligonucleotides having 2 up to 10 nucleosides which are linked to each other via both 3'-5' and via 5'-3' phosphoric acid ester bonds. However, the nucleotides according to the invention additionally comprise polynucleotides having more than 10 nucleoside building blocks.

The nucleoside derivatives according to the invention can be synthesized by a multi-step or by a two-step synthesis. Typically, the desired ring system is first synthesized with the corresponding substitution pattern in which an alcohol of the general formula

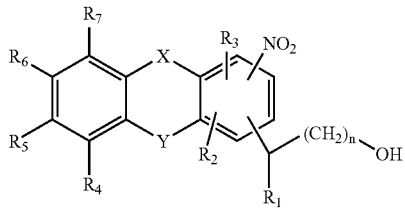

is initially produced by a generally known synthesis method, wherein $R_1$ to $R_7$, X, Y and n are as defined above. In a second step, this alcohol is converted into an acylation reagent by means of methods known from literature, e.g. into a chlorocarbonic ester, e.g. using diphosgene, into a chlorothiocarbonic ester, e.g. using thiophosgene, or into a sulfonyl chloride. Thereafter, a correspondingly derivatized nucleoside, e.g. thymidine, is acylated with this acylation reagent, to result in the nucleoside derivative according to the invention.

A possibility of carrying out the process according to the invention is explained by way of example on the basis of FIG. 1.

The free nucleoside for use in processes according to the invention initially has preferably two free OH groups, one at the 3' position and the other at the 5' position. Thereafter, one of them is protected intermediately at the 3' or 5' position by introducing an orthogonal protecting group, e.g. DMT or dansyl such that the remaining free hydroxyl group (5' or 3') can react with the acylation reagent. Where necessary, the intermediate protecting group may be cleaved such that the free 3' or 5' OH group is available for further reactions.

Further advantages and embodiments of the invention follow from the description and the enclosed figures.

It is understood that the above mentioned features and the features to be explained below cannot only be used in the respectively given combination but also in other combinations or as such without departing from the scope of the present invention.

The invention is explained below by means of the subsequent figures and a non-limiting embodiment.

FIG. 1 shows a synthesis scheme for the production of a nucleoside derivative according to the invention, FIG. 2 shows a comparison between the reaction rate in the cleavage of the protecting group (deprotection reaction) of a nucleoside derivative of the prior art and a nucleosicde derivative according to the invention, FIG. 3 shows the rate of the protecting group cleavage from a nucleoside derivative according to the invention in various solvents.

The quantitative decrease in the educt over the reaction period of the cleavage reaction was measured with both compounds at a wavelength of 365 nm (Hg lamp) in a methanol/water mixture.

Figure 2:
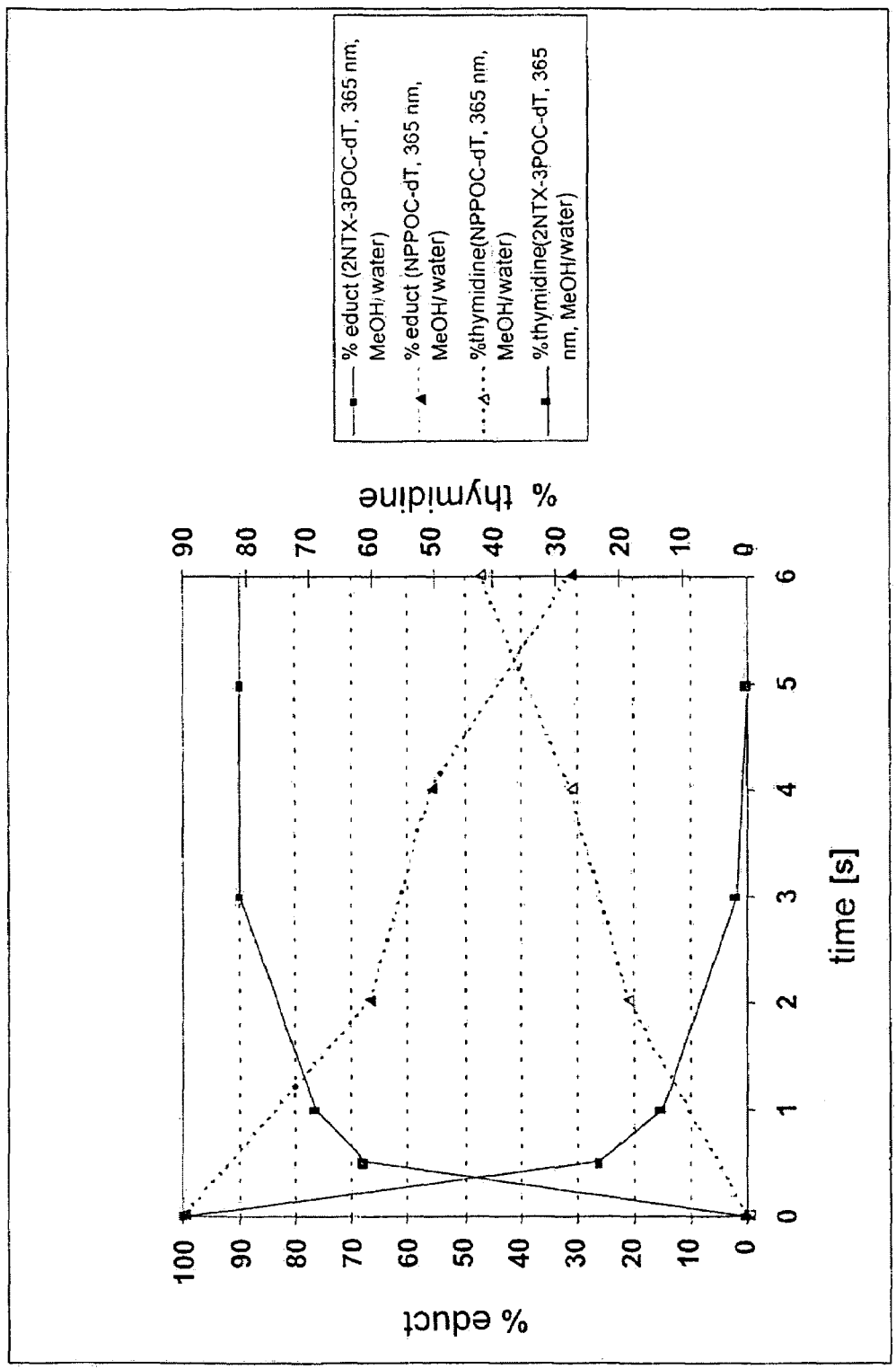
FIG. 2 shows the reaction rate occurring when the protecting group of a prior art nucleoside derivative, NPPOC thymidine (NPPOC-dT), is cleaved, as compared to a nucleoside derivative according to the invention, 2-NTX-3-POC-thymidine(2-NTX-3POC-dT)(5'-[2-nitro-9-oxo-3-(2-propyloxacarbonyl)thioxanthone]thymidine).

As is evident from FIG. 2, the decrease in educt concentration proceeds with 2-NTX-3POC-dT in curve 1 markedly faster than in educt NPPOC-dT (curve 2). This correlates very well with the increase in educt in the corresponding curves 3 and 4.

In the case of 2-NTX-3POC as photolabile protecting group, 90% product were obtained after a reaction period of only about 3 seconds while only 40% thymidine were obtained with NPPOC after a reaction period of 6 second, which is twice as long.

Figure 3:
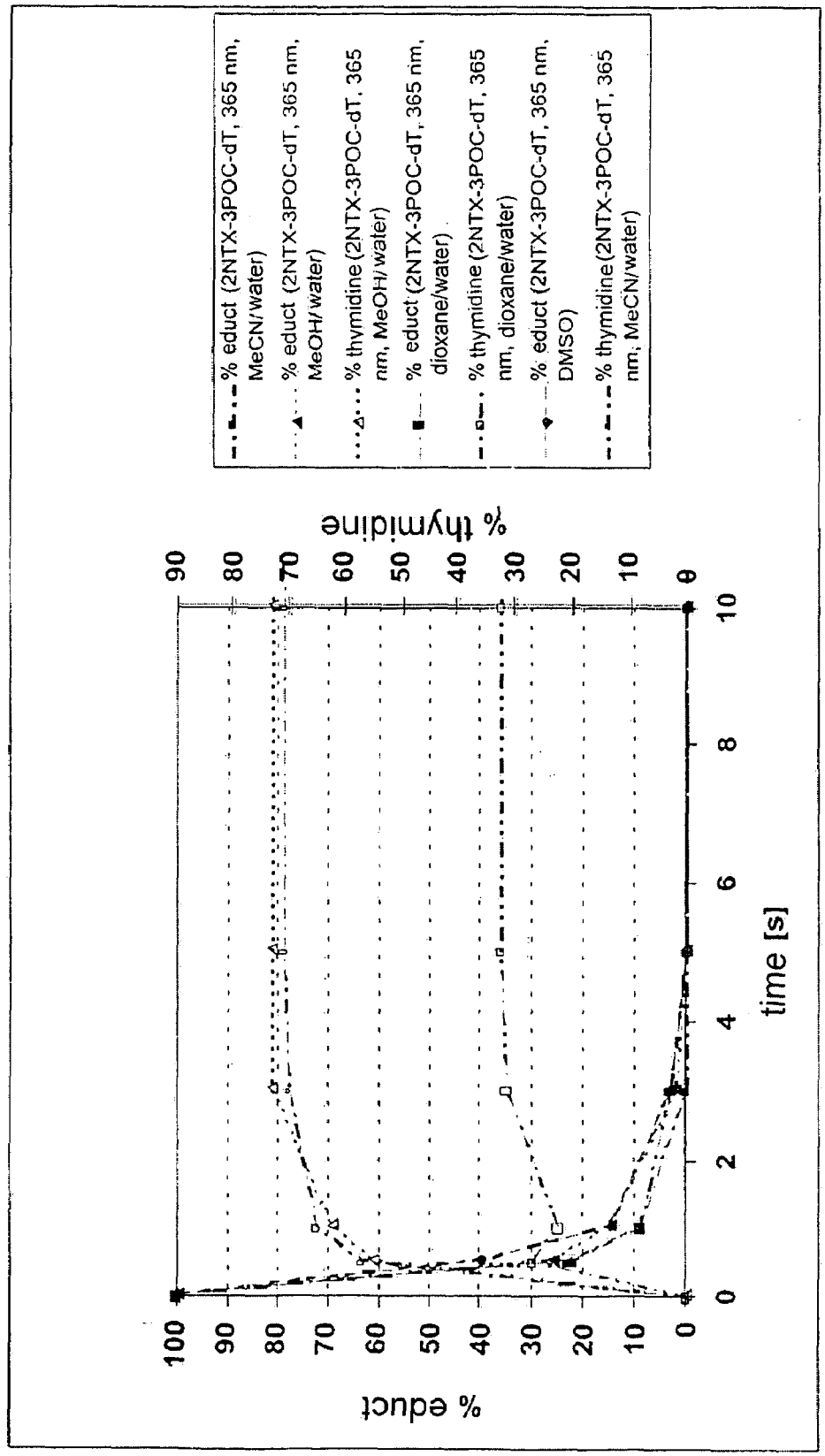

FIG. 3 shows the reaction course of the cleavage of the photolabile protecting group from 2-NTX-3-POC-dT in various solvents at 365 nm (Hg lamp, UG 1 filter) with respect to the decrease in educt 2-NTX-3-POC-dT and also with respect to the increase in the thymidine product.

Except for the reaction in dioxane/water, the reaction rates in the mixtures acetonitrile/water or methanol/water are approximately equally fast.

Figure 4:
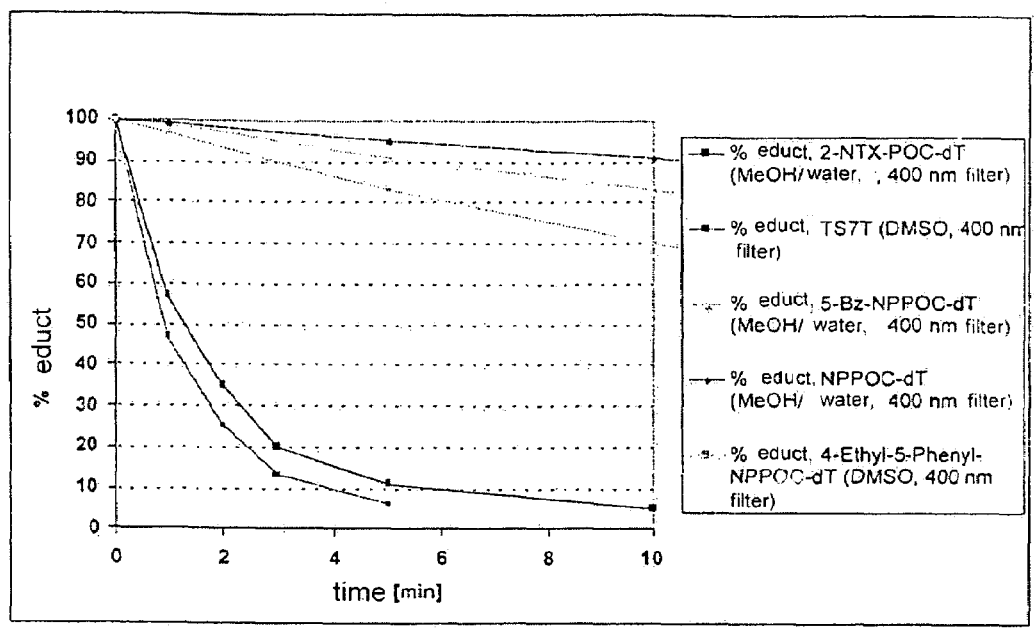
FIG. 4 shows the rate of deprotection reaction at a wavelength above 390 nm.

FIG. 4 shows the deprotection reaction rate when the protecting group according to the invention of a nucleoside derivative is cleaved (in each case with thymidine) as compared to protecting groups from the prior art at wavelengths above 390 nm. In comparison with the protecting groups NPPOC, 5-benzyl (Bz)-NPPOC and 4-ethyl-5-phenyl-NPPOC, the deprotection reaction rate is the fastest with protecting groups 2-NTX-3-POC or TS7POC (5'O-[(2-nitrophenyl)-5-(9-oxo-9H-thioxanthone-2-yl)pentyloxycarbonyl]).

Protecting group 2-NTX-3-POC according to the invention is somewhat slower as compared to TS7POC at a wavelength of 400 nm up to a reaction period of about 4 minutes and reaches approximately the same values as TS7POC.

In contrast to the protecting group according to the invention TS7POC uses the principle of what is called "intramolecular activation" of the protecting group where a sensitizer unit is bound to a conventional protecting group (as described in PCT/EP 2004/002361, for example). Surprisingly, it turned out in the present case that U.V. sensitizers formerly considered indispensable for rapid reaction times in the deprotection reaction can be dispensed with, i.e. both an intramolecularly bound sensitizer, such as in TS7POC, and a separately added sensitizer as described in WO 03/74542, for example, to increase the reaction rate of the cleavage reaction. Nevertheless, reaction rates comparable to those achieved in the presence of sensitizers for the cleavage reaction are obtained with the derivatives or protecting groups according to the invention.

Figure 5:
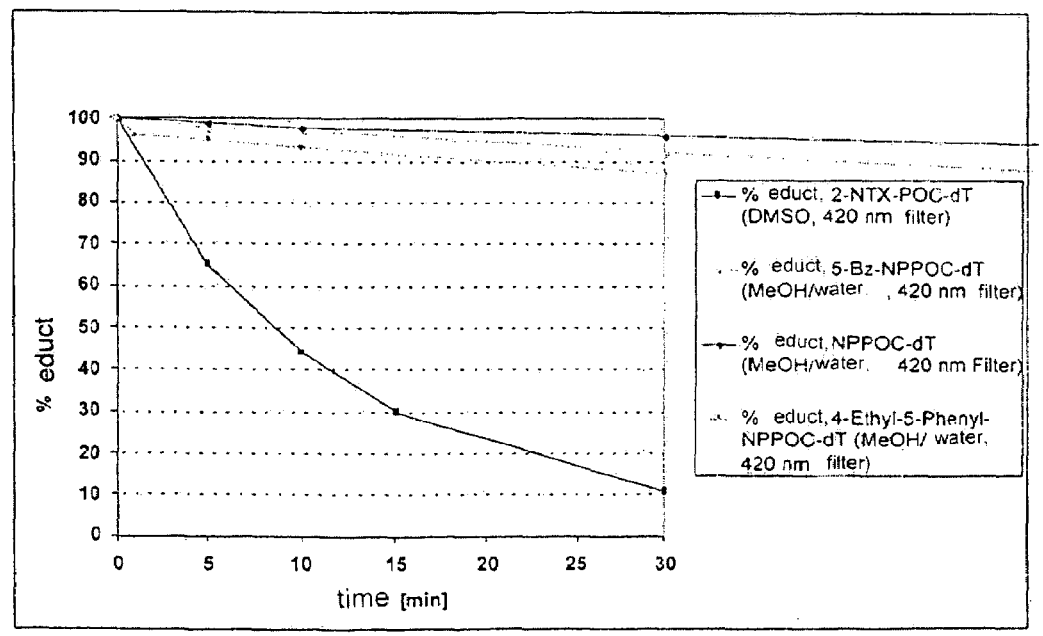
FIG. 5 shows the rate of the deprotection reaction at a wavelength above 410 nm.

FIG. 5 shows that when a protecting group according to the invention, namely 2-NTX-3-POC, is used, the cleavage rate at 420 nm is considerable compared to the conventional protecting groups known from the prior art and a cleavage of 90% has occurred after a reaction period of about 30 minutes while almost no reaction can be seen with the prior art protecting groups.

EXAMPLE

Figure 1:
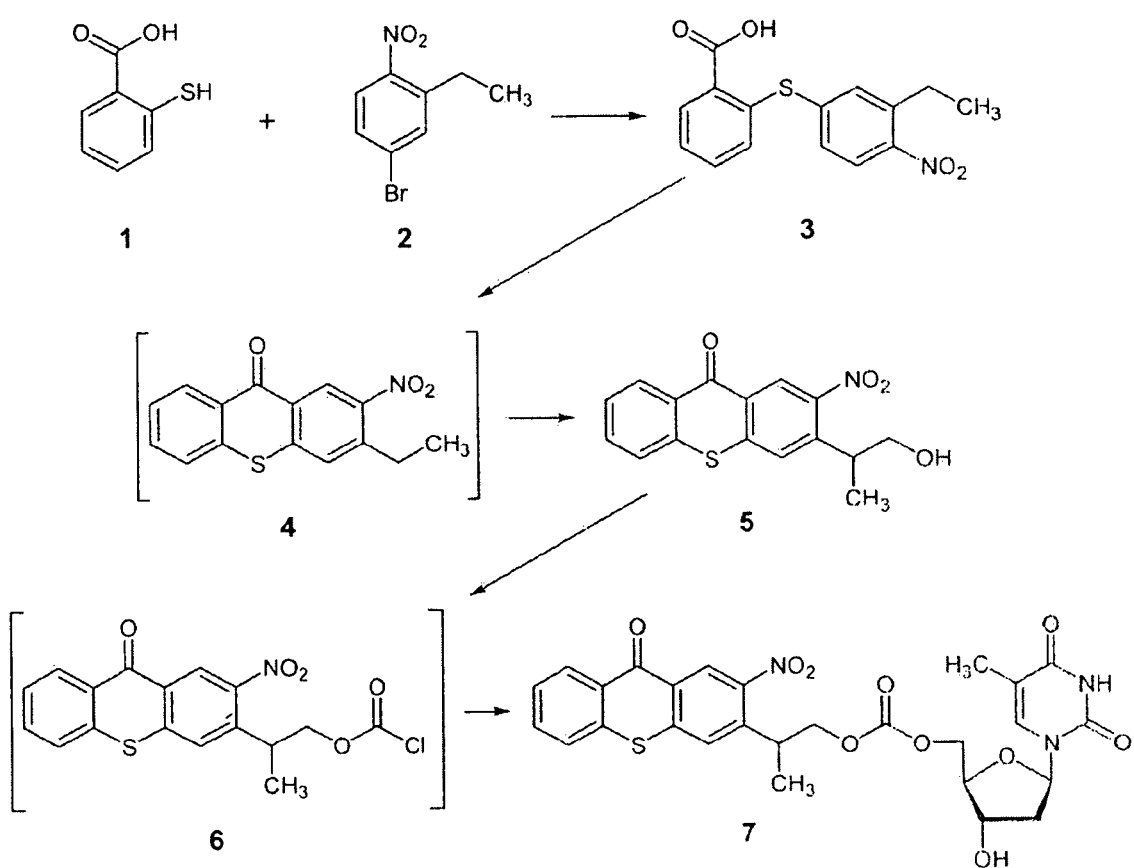

Synthesis of 5λ-[2-nitro-9-oxo-3-(2-propyloxycarbonyl)-thioxanthone]thymidine The synthesis of the title compound is explained schematically in FIG. 1. The reaction of thioacetylic acid 1 with (2-nitro-5-bromo)ethylbenzene 2 in boiling DMF in the presence of 1,8-diazabicyclo[5,4,0]undec-7-ene (DBU) results in the formation of 2-(3-ethyl-4-nitrophenylsulfide)benzoic acid 3, which was isolated as a solid with a yield of 70 to 80%. The heating of the benzoic acid 3 in concentrated sulphuric acid over a period of 0.5 to 1 hour followed by the addition of the reaction mixture in water and filtration yielded 3-ethyl-2-nitro-9-oxothioxanthone 4 which was used for the next step without further purification. The reaction of the nitro derivative of oxothioxanthone 4 from the preceding step with paraformaldehyde in DMSO in the presence of DBU at 60 to 70° C. for 4 to 5 hours yielded 4-nitro-9-oxo-3-(2-propanol)thioxanthone 5 which was isolated in good yields by means of column chromatography. The treatment of compound 5 with disphosgene in THF at 0 to 4° C. in the presence of triethylamine yielded 2-nitro-9-oxo-3-(2-propyloxycarbonyl-chloride)thioxanthone 6 in good yield. The acylation of thymidine with compound 6 at 0 to 4° C. results in 5'-[2-nitro-9-oxo-3-(2-propyloxacarbonyl)thioxanthone]thymidine 7 which was isolated by column chromatography.

Spectroscopic data for compound 5:

UV (MeOH), $\lambda_{max}$ in nm (log $\epsilon$): 359 (3.86), 252 (4.48), 212 (4.12). $^1$H-NMR (DMSO-D$_6$): 8.72 (s, H—C(1)); 8.42 (dd, H—C(8)); 8.03 (s, H—C(4)); 7.86 (dd, H—C(5)); 7.99 (ddd, H—C(7)); 7.61 (m, H—C(6)).

Spectroscopic data for compound 6:

UV (MeOH), $\lambda_{max}$ in nm (log $\epsilon$): 348 (3.87), 254 (4.54), 211 (4.27). $^1$H-NMR (DMSO-D$_6$): 11.14 (s, NH); 8.40 (dd, H—C(8*)); 8.15 (s, H—C(4*)); 7.85 (dd, H—C(5*)); 7.78

(ddd, H—C(7*)); 7.60 (ddd, H—C(6*)); 7.34 (s, H—C(6)); 6.11 (m, H—C(1')); 5.33 (d, OH); 4.41 (m, 2H, CH$_2$ for the 5' protecting group); 4.24 (m, 2H, H—C(5',5")); 4.18 (m, H—C(3')); 3.87 (m, H—C(4')); 3.75 (q, CH$_3$CH); 2.10 (m, 2H, H—C(2',2")); 1.70 and 1.69 (2s, CH$_3$—C(5)); 1.38 (d, CH$_3$CH).

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosure of all applications, patents and publications, cited herein and of corresponding German application No. 102004019098.4, filed Apr. 20, 2004 is incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A nucleoside derivatives having a photolabile protecting groups of the formula (I)

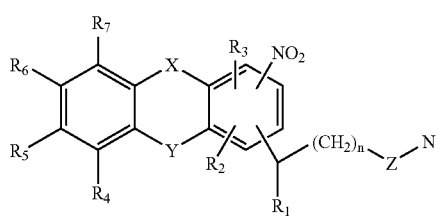

wherein R$^1$=H, halogen, NO$_2$, CN, OCH$_3$, an alkyl, alkoxy or alkoxyalkyl residue having 1 to 4 C atoms, or an optionally substituted aryl residue or aliphatic acyl residue having 2 to 5 atoms, R$^2$ to R$^7$=H, NO$_2$, CN, OCH$_3$, a branched or unbranched alkyl, alkoxy or alkoxyalkyl residue having 1 to 5 C atoms or an optionally substituted aryl residue or an aliphatic acyl residue having 2 to 5 atoms, X is C=O or C=S, Y=S, O, NR', C(R')$_2$, wherein R' is H, or a branched or unbranched alkyl residue having 1 to 5 C atoms or an optionally substituted aryl residue, Z=SO$_2$, OCO, OCS, SCS, CO or CS, n=0, 1, 2 or 3 with the proviso that when n=0, Z is CO, CS, or SO$_2$, N is

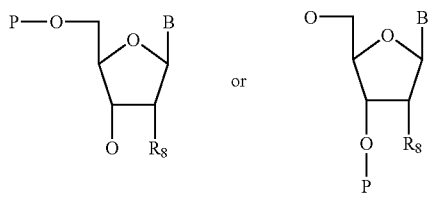

wherein P=H or a protecting group common in nucleotide chemistry or a common reactive group for the production of oligonucleotides, B=adenine, cytosine, guanine, thymine, uracil, 2,6-diaminopurine-9-yl, 5-methylcytosinyl-1-yl, 5-amino-4-imidazolecarboxylic acid-1-yl or 5-amino-4-imidazolecarboxylic acid amide-3-yl, wherein when B=adenine, cytosine or guanine having a primary amino function it optionally has a temporary or permanent protecting group thereon, and when B=thymine or uracil, the O$^4$ position optionally has a permanent protecting group, R$_8$=H, OH, halogen, OR' or SR', wherein R' is as defined above, or an aliphatic acyl residue having 2 to 5 c atoms or a protecting group common in nucleotide chemistry.

2. The nucleoside derivative according to claim 1, wherein an NO$_2$ group and the —C(R$_1$)—(CH$_2$)n-Z-N group are placed in the ortho position relative to each other.

3. The nucleoside derivative according to claim 1, wherein the common reactive group for the production of oligonucleotides in the P position is a phosphitamide group.

4. A process for the production of a nucleoside derivatives according to claim 1, comprising reacting a) a compound of general formula II

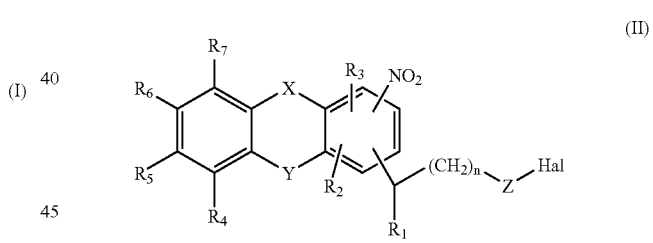

wherein the residues are as defined in claim 1, with a nucleoside of general formula III

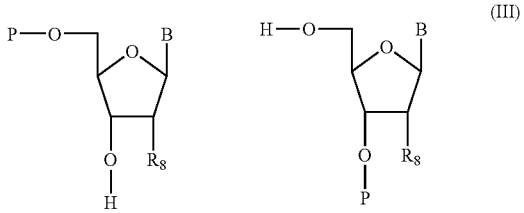

wherein R$_8$ and B are as defined in claim 1 and wherein P is a protecting group common in nucleotide chemistry, and b) P is reacted further, where appropriate.

5. The process according to claim 4, wherein a phosphitamide group is introduced in the 5' position or 3' position of the resulting nucleoside derivatives.

6. A method for synthesizing an oligonucleotide or nucleic acid chip, comprising performing light controlled synthesis employing the nucleoside derivative of claim 1 to produce oligonucleotides or nucleic acid chips.

7. Use according to claim 6, wherein light having a wavelength of above 380 nm is used.

8. A nucleoside of claim 1 wherein $R^1$ is methyl, ethyl, propyl or butyl.

9. A method of claim 7 wherein said wavelength is above 390 mm.

* * * * *

UNITED STATES PATENT AND TRADEMARK OFFICE
CERTIFICATE OF CORRECTION

PATENT NO. : 7,432,368 B2 Page 1 of 1
APPLICATION NO. : 11/109873
DATED : October 7, 2008
INVENTOR(S) : Klaus-Peter Stengele It is certified that error appears in the above-identified patent and that said Letters Patent is hereby corrected as shown below:

Column 10, line 20, after "function", insert -- , --.

Column 11, line 5, reads "Use", should read -- A method --.

Signed and Sealed this

Tenth Day of February, 2009

JOHN DOLL
*Acting Director of the United States Patent and Trademark Office*